United States Patent
Ali et al.

(10) Patent No.: US 9,738,570 B1
(45) Date of Patent: *Aug. 22, 2017

(54) METHOD FOR METHANOL CONVERSION TO PROPYLENE OVER A MONOLITHIC CATALYST SYSTEM

(71) Applicant: KING FAHD UNIVERSITY OF PETROLEUM AND MINERALS, Dhahran (SA)

(72) Inventors: Mohammad Ashraf Ali, Dhahran (SA); Shakeel Ahmed, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/492,567

(22) Filed: Apr. 20, 2017

Related U.S. Application Data

(63) Continuation of application No. 15/065,479, filed on Mar. 9, 2016, now Pat. No. 9,675,971, which is a continuation-in-part of application No. 14/520,978, filed on Oct. 22, 2014, now Pat. No. 9,682,367.

(51) Int. Cl.
*B01J 29/06* (2006.01)
*B01J 29/70* (2006.01)
(Continued)

(52) U.S. Cl.
CPC ............... *C07C 1/20* (2013.01); *B01J 29/06* (2013.01); *B01J 35/0013* (2013.01); *B01J 35/023* (2013.01); *B01J 35/04* (2013.01); *B01J 35/1019* (2013.01); *B01J 35/1023* (2013.01); *C07C 2529/06* (2013.01)

(58) Field of Classification Search
None
See application file for complete search history.

(56) References Cited

U.S. PATENT DOCUMENTS

| 4,311,865 A | 1/1982 | Chen |
|---|---|---|
| 2006/0189476 A1 | 8/2006 | Deckman |
| 2013/0059723 A1 | 3/2013 | Yilmaz |

FOREIGN PATENT DOCUMENTS

| CN | 101433858 A | 5/2009 |
|---|---|---|
| CN | 101407441 B | 6/2012 |

(Continued)

OTHER PUBLICATIONS

BaiBing Yang, "Preparation of Modified ZSM-5/Cordierite Monolithic Catalyst and Their Catalytic Performance of Methanol to Olefin", Chemical Engineering and Technology, 2011, 2 pages.

(Continued)

*Primary Examiner* — Colin W Slifka
(74) *Attorney, Agent, or Firm* — Oblon, McClelland, Maier & Neustadt, L.L.P.

(57) ABSTRACT

A catalyst system and a process for methanol to light olefin conversion with enhanced selectivity towards propylene. The catalyst system comprises a honeycomb monolith catalyst support coated with aluminosilicate nanozeolite catalysts on the edges and inside the channels of the support structure. The aluminosilicate nanozeolite catalysts have not been pre-modified with a promoter metal. The catalyst system gives higher hydrothermal stability to the catalyst compared to randomly packed pellet catalysts and allows methanol to be converted to predominantly propylene at a low temperature, with decreased selectivity towards $C_2$, higher olefins and paraffinic hydrocarbons.

7 Claims, 3 Drawing Sheets

(51) Int. Cl.
*B01J 29/40*  (2006.01)
*B01J 35/04*  (2006.01)
*B01J 35/00*  (2006.01)
*B01J 38/12*  (2006.01)
*C07C 1/20*  (2006.01)
*B01J 35/10*  (2006.01)
*B01J 35/02*  (2006.01)

(56) References Cited

FOREIGN PATENT DOCUMENTS

| CN | 102531823 A | 7/2012 |
|---|---|---|
| CN | 103242125 B | 12/2014 |
| CN | 104226360 A | 12/2014 |
| JP | 5744730 B2 | 5/2015 |
| WO | WO 2014/001412 A2 | 1/2014 |

OTHER PUBLICATIONS

Javad Ahmadpour, et al., "Catalytic conversion of methanol to propylene over high-silica mesoporous ZSM-5 zeolites prepared by different combinations of mesogenous templates", Journal of Natural Gas Science and Engineering, vol. 23, 2015, pp. 184-194.

Qian Wang, et al., "Effect of $SiO_2/Al_2O_3$ ratio on the conversion of methanol to olefins over molecular sieve catalysts", Frontiers of Chemical Science and Engineering, vol. 5, Issue 1, Mar. 2011, pp. 79-88 (Abstract only).

M. Firoozi, et al., "The effect of micro and nano particle sizes of H-ZSM-5 on the selectivity of MTP reaction", Catalysis Communications, vol. 10, Issue 12, Jun. 25, 2009, pp. 1582-1585 (Abstract only).

METHOD FOR METHANOL CONVERSION TO PROPYLENE OVER A MONOLITHIC CATALYST SYSTEM

CROSS REFERENCE TO RELATED APPLICATIONS

The present application is a continuation of U.S. Pat. No. 9,675,971, which is a continuation-in-part of U.S. Pat. No. 9,682,367.

BACKGROUND OF THE INVENTION

Technical Field

The present invention relates to a process and a catalyst system for converting methanol into light olefins. More specifically, the process and the catalyst system increase the selectivity of the methanol conversion to propylene.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Increasing cost and uncertain supply of crude oil has prompted the search for alternative processes for producing hydrocarbon products. One such process is the conversion of methanol into light olefins such as ethylene, propylene and butylenes. There is a specific interest in the use of methanol to produce light olefins due to the fact that methanol is being produced worldwide in large quantity from natural gas through the production of synthesis gas (mixture of CO and $H_2$) from methane gas which is then converted to methanol. Methanol can also be produced from coal and biomass processing. Methanol is converted commercially into propylene using randomly packed pellet catalysts. This process has limitations, such as lower selectivity to propylene and higher yields of byproducts such as $C_2$, $C_4$ $C_5$ and higher olefins and paraffinic hydrocarbons.

Processes for converting methanol to light olefins are well known in the prior art. Early catalysts used for this conversion reaction were based on aluminosilicate molecular sieves. These processes have been described in U.S. Pat. Nos. 4,238,631, 4,328,384, 4,423,274 and 4,499,327 (each incorporated herein by reference in its entirety). These patents reveal the deposition of coke onto the molecular sieves in order to increase selectivity to light olefins and minimize the formation of $C_5$ and higher hydrocarbons as byproducts. The effect of the coke is to reduce the effective pore diameter of the molecular sieves. The prior art also disclose that silicoaluminophosphate molecular sieves can be used to catalyze the methanol to olefin process. The U.S. Pat. No. 4,499,327 discloses that a number and variety of silicoaluminophosphate molecular sieves can be used to convert methanol to olefins.

Propylene is perhaps one of the oldest and most important of the crucial building blocks of the petrochemical industry and one of the principal light olefins. From propylene, important industrial derivatives such as polypropylene, acrylonitrile, propylene oxide, 2-propanol, cumene/phenol, oxo-alcohols, isopropanol, acrylic acids, and oligomers are obtained. Various additional products use propylene as a feedstock. Hence, its use can be seen to span a wide range of end-use industries, from automotive and construction, to polymers, consumer durables, packaging, medical devices, and electronics.

Historically, propylene was readily available, either as a co-product of heavy liquids cracking or from refinery sources. Growth in demand for propylene derivatives has outpaced that for ethylene derivatives for several years. The higher propylene demand has largely absorbed readily available sources of propylene to yield, until now, a fairly balanced global market in terms of propylene supply and demand. However, an interesting dynamic is now unfolding in the United States whereby large amounts of natural gas from shale and other sources are being produced with their accompanying natural gas liquids (NGLs) such as ethane, propane and butanes. This additional NGL is being utilized in higher percentages in steam crackers, which in turn, is lowering available propylene supplies and changing the competitiveness of the North American ethylene chain.

With the recent discovery of U.S. shale gas reserves and the increase in ethane cracking currently taking place that is set to only increase exponentially in coming years, the U.S. propylene supply has tightened by large amounts. This is because the cracking of light feedstocks produces dramatically less propylene co-product than the cracking of heavy liquids. Consequently, propylene production in the United States from ethylene crackers has declined, and, for the first time in 20 years, propylene prices were higher than ethylene prices. This propylene supply/demand gap is projected to considerably widen in the next few years as propylene demand rises and even greater volumes of lighter feedstocks available from shale gas deposits rapidly replace heavy liquids in crackers. LPG cracking in Europe will have a similar impact, although the displacement of hydrocarbon liquids will not be nearly as pronounced as in North America. Hence, shortages of propylene feedstock are likely in these two regions—imbalances which will extend to other regions via higher propylene pricing.

In view of the forgoing, one object of the present disclosure is to provide a catalyst system comprising a honeycomb monolith structure loaded with aluminosilicate zeolite nanoparticles for the conversion of methanol into light olefins having improved selectivity towards propylene and lower yields of byproducts such as $C_2$, $C_4$, $C_5$ and higher hydrocarbons. Additional objects of the present disclosure are to provide a process for conversion of methanol into light olefins having improved selectivity towards propylene employing the catalyst system as well as a method of preparing the catalyst system.

BRIEF SUMMARY OF THE INVENTION

According to a first aspect, the present disclosure relates to a catalyst system comprising i) zeolite nanoparticles, and ii) a honeycomb monolith support coated with the zeolite nanoparticles on the edges and inside the channels of the honeycomb monolith support, wherein the zeolite nanoparticles are not modified with a promoter metal.

In one embodiment, the zeolite nanoparticles are microporous molecular sieves having an MFI framework type.

In one embodiment, the zeolite nanoparticles have a silica to alumina ratio in the range of 20 to 5000.

In one embodiment, the zeolite nanoparticles have a silica to alumina ratio in the range of 20 to 300.

In one embodiment, the honeycomb monolith support comprises 400-1200 cells per square inch.

In one embodiment, the honeycomb monolith support comprises cells having an average height of 0.5-2.0 inches and an average width of 0.5-2.0 inches.

In one embodiment, the catalyst system further comprises a binder.

In one embodiment, the zeolite nanoparticles further comprise an alkaline earth metal.

According to a second aspect, the present disclosure relates to a process for converting methanol into light olefins, comprising contacting methanol in a reactor with the catalyst system to form at least one light olefin selected from the group consisting of ethylene, propylene and butene.

In one embodiment, the conversion selectivity towards propylene is in the range of 30-90% of the total mass of the products.

In one embodiment, the weight ratio of propylene to ethylene in the products is greater than 4.0.

In one embodiment, the methanol is in the vapor phase.

In one embodiment, the contacting is carried out at a pressure in the range of 0-50 psig.

In one embodiment, the contacting is carried out in the presence of an inert gas and the ratio of inert gas to hydrocarbon is in the range of 0.1-1.0.

In one embodiment, the reactor is at least one selected from the group consisting of a fixed-bed reactor and a moving-bed reactor.

In one embodiment, the conversion selectivity towards propylene relative to the total mass of products is greater than a substantially similar process performed with substantially similar zeolite nanoparticles lacking the honeycomb monolith support.

In one embodiment, the weight ratio of propylene to ethylene in the products is greater than a substantially similar process performed with substantially similar zeolite nanoparticles lacking the honeycomb monolith support.

According to a third aspect, the present disclosure relates to a method of preparing the catalyst system comprising i) reacting and aluminate and a silicate and/or orthosilicate in the presence of a base to form zeolite nanoparticles having a silica to alumina molar ratio in the range of 20-5000, ii) coating the honeycomb monolith with the zeolite nanoparticles on the edges and inside the channels of the honeycomb monolith, and iii) calcining the honeycomb monolith coated with zeolite nanoparticles, wherein the zeolite nanoparticles are microporous molecular sieves having an WI framework type, and wherein the honeycomb monolith comprises 400-1200 cells per square inch and cells that have an average height of 0.5-2.0 inches and an average width of 0.5-2.0 inches.

In one embodiment, the aluminate is sodium aluminate, the silicate and/or orthosilicate is tetraethyl orthosilicate, and the base is tetrapropyl ammonium hydroxide.

In one embodiment, the method further comprises mixing the zeolite nanoparticles having a silica to alumina molar ratio in the range of 20-5000 with a binder prior to the coating and coating the honeycomb monolith with the zeolite nanoparticles and the binder on the edges and inside the channels of the honeycomb monolith

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1A is a schematic diagram illustrating a monolith honeycomb structure with nanozeolite coating.

FIG. 1B is an expanded view of a schematic diagram illustrating a cell of a monolith honeycomb structure with nanozeolite coating.

DETAILED DESCRIPTION OF THE EMBODIMENTS

Figure 1C:
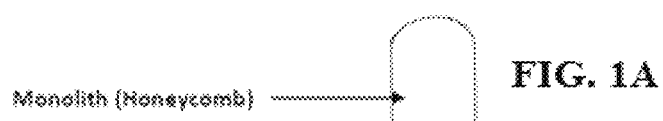
FIG. 1C is an expanded view of a schematic diagram illustrating a coating layer of nanozeolite on the edges and inside the channels of the honeycomb monolith support.

Embodiments of the present disclosure will now be described more fully hereinafter with reference to accompanying drawings, in which some, but not all embodiments of the disclosure are shown.

The present invention pertains to a catalyst system or a catalytic composite comprising a honeycomb monolith catalyst support or carrier loaded with aluminosilicate nanozeolite catalysts (see FIG. 1) for methanol conversion into light olefins at low pressure, with high selectivity towards propylene and low selectivity towards $C_2$, $C_4$, $C_5$ and higher olefins, paraffins and other hydrocarbon byproducts. In other words, the catalyst system or catalytic composite of the present invention is effective in converting methanol into predominantly propylene, i.e. at least 40% of the total mass of products, preferably 50-70%, even more preferably 60-80%.

For purposes of the present invention, "catalyst system" and "catalytic composite" refer to materials such as an initiator or a catalyst, optionally an activator or a promoter that enhances the activity of the catalyst, a catalyst support or a carrier for the mounting or loading of the catalyst and the promoter, and optionally a binder that enhances the loading of the catalyst and the optional promoter onto the catalyst support. These materials, in combination, cause chemical reactions to begin. Optional promoters may be part of the catalysts, for example, being adsorbed to the surface of catalyst particles. The catalyst support is usually inert towards the catalyzed reaction. In a preferred embodiment, the catalyst, the optional promoter, the optional binder are loaded only on the exterior surface of the catalyst support.

In a most preferred embodiment, the catalyst system consists essentially of the catalyst comprising zeolite nanoparticles that are not modified with a metal promoter loaded and/or coated on the edges and inside the channels of the exterior surface of the monolith honeycomb support For purposes of the present invention, "light olefins" refers to ethylene, propylene and butylene.

The monolithic-nanozeolite catalyst system according to the present invention may be used in methanol-based propylene production facilities as well as in existing methanol to propylene conversion units.

Other petrochemical catalytic reactions that are conducted on randomly packed pellet catalyst systems may also benefit from the monolithic catalyst support structure loaded with aluminosilicate zeolite nanoparticles and optionally metal-modified or metal-promoted aluminosilicate nanozeolite crystals. This is especially true for petrochemical reactions wherein selectivity towards certain products is desired and large gas volumes are to be treated. The honeycomb monolith structure comprising a large number of parallel channels provides high contact efficiencies between the monolith and gas flow streams, offers a very low pressure drop, short diffusion lengths and no obstruction by particulate matter. The monolithic-nanozeolite catalyst system offers improved propylene selectivity by providing easy and ordered access to the reactants and products through a decrease in diffusion limitations. The diffusion limitation of monolithic-nanozeolite catalyst systems can be significantly reduced as compared to randomly packed pellet catalysts.

As used herein "aluminosilicate nanozeolites", "alumino silicate zeolite nanoparticles", "zeolite nanoparticles", "nanozeolites" or "nanozeolite crystals" refer to microporous aluminosilicate minerals. These minerals are commonly used as commercial adsorbents and catalysts. In some embodiments, the zeolite nanoparticles may be Zeolite Socony Mobil-5 (framework type MFI from ZSM-5 (five)), an aluminosilicate zeolite belonging to the pentasil family of zeolites having a chemical formula of $Na_nAl_nSi_{96-n}O_{192}.16H_2O$ (0<n<27). In certain embodiments, the zeolite nanoparticles have a silica to alumina molar ratio in the range of 20-5000, preferably 30-2500, preferably 40-2000, preferably 50-15000, preferably 60-1000, preferably 70-800, preferably 80-600, preferably 90-400, preferably 100-300. In a preferred embodiment, the zeolite nanoparticles have a silica to alumina molar ratio in the range of 20-300, preferably 30-290, preferably 80-280, preferably 100-260.

In certain embodiments, the nanozeolites may further comprise a metal promoter or metal modifier. The metal for modification or promotion of nanozeolites, of the catalyst promoter, is a rare earth metal selected from, but not limited to, the group consisting of iron, cobalt, nickel, chromium and combinations thereof. In one embodiment, the metal particles are nanoparticles, with an average particle diameter of 1-10 nm, preferably no greater than 5 nm, and preferably having an average particle diameter of 2-4 nm. The amount of promoter metal in the catalyst may be 5-15 wt. % of the total weight of the catalyst system, with the remaining weight attributed to the monolithic catalyst support and nanozeolites. In another embodiment, the amount of non-modified aluminosilicate nanozeolites may be preferably 7-12 wt. % of the catalyst system, even more preferably 8-10 wt. %.

Similarly, the nanozeolite crystals have an average particle diameter of no greater than 100 nm, preferably 10-100 nm, preferably having an average particle diameter of 50-85 nm, more preferably 10-70 nm, even more preferably 10-50 nm. The particle size distribution of the nanozeolites is such that more than 95%, preferably more than 98% or more than 99% of the particles have a particle size of less than 50 nm. The zeolite crystals are preferably no greater than 100 nm as large crystals tend to further crack the propylene formed, thus causing the reaction to lose propylene selectivity.

In certain embodiments, the nanozeolite crystals may be modified by wetness impregnation method using a solution containing one of the aforementioned metals. The impregnation process may involve a plurality of precursor and intermediate compounds.

Preferably, the nanozeolite catalysts are molecular sieves on the edges and inside the channels of the honeycomb monolith support, with three-dimensional microporous MFI framework structure of $Al_2O_3$ and $SiO_2$ tetrahedral units, for example, ZSM-5 in its H-form. As used herein, the molecular sieves have pore diameters of less than 2 nm. The zeolites are a unique group of molecular sieves that are structured as a lattice of silica and optionally alumina, and are protonic with exchangeable cations such as alkali or alkaline earth metal ions. Zeolites have a porous structure that can accommodate a wide variety of cations, such as $Na^+$, $K^+$, $Ca^{2+}$, $Mg^{2+}$ and others. In one embodiment, the zeolite nanoparticles further comprise an alkaline earth metal. These positive ions are rather loosely held and can readily be exchanged. These alkaline earth metals are distinguishable from additionally optional rare earth metal promoters that that enhances the activity of the catalyst. Examples of these alkaline earth metal ions include magnesium (Mg), beryllium (Be), calcium (Ca), strontium (Sr), barium (Ba) and radium (Ra). The term zeolite also included technically and structurally related materials similar to zeolites but in which the silica and alumina may be replaced totally or partially with other oxides.

It may be advantageous to incorporate catalyst promoter with the catalyst or into the monolith support structure. Promoters function as co-catalysts and increase the overall catalytic activity of the catalyst and product selectivity with little increase in overall catalysis costs. Suitable promoters may be selected from a wide variety of rare earth metals as previously described. One promoter that has been found to be particularly effective is iron, and a particularly effective combination is the use of iron promoter with ZSM-5 zeolite catalyst. This catalyst-promoter combination may be used to impregnate a cordierite monolith support for use in the methanol to propylene reaction according to the present invention. The catalyst-promoter combination may be co-extruded with the monolith support material.

The nanozeolite crystals may be evaluated by characterizing and comparing the physical and chemical properties of the crystals. Physical properties such as morphology, surface area, dispersion and composition may be characterized using different techniques, for example, scanning electron microscopy (SEM), thermo-gravimetric analysis (TGA), X-ray diffraction (XRD) and energy dispersive X-ray spectroscopy), differential scanning calorimetry (DSC), Brunauer-Emmett-Teller (BET) adsorption and Fourier transform infrared (FTIR).

The BET surface area of the obtained aluminosilicate nanozeolite crystals is 100-1000 $m^2g^{-1}$, preferably 200-800 $m^2g^{-1}$, or 300-600 $m^2g^{-1}$. The unmodified nanozeolite crystals have a BET surface area of 100-300 $m^2g^{-1}$.

The pore size distribution of the aluminosilicate nanozeolites is 0.6-1.0 nm, preferably 0.7-0.8 nm.

The monolith structure loaded on edges and inside channels, with aluminosilicate MFI type catalyst, of this invention may be mixed with a binder to provide better loading on the monolith structure. Examples of the binders that can be used include alumina, silica, aluminum-phosphate, silica-alumina, and their mixtures. Preferably, the binder is present only on the exterior surface of the nanozeolite crystals and the honeycomb monolith support. Preferably the aluminosilicate zeolite nanoparticles are present only on the surfaces of the monolith structure (including within the monolith structure channels) and not incorporated within the support material used to make the monolith structure.

The conversion of methanol to light olefins is effected by contacting the methanol with the monolith structure loaded with aluminosilicate nanozeolite molecular sieve catalyst at conversion conditions, thus forming the desired light olefins. The methanol may be in the liquid or vapor phase. Preferably, the methanol is in the vapor phase. Contacting the methanol with honeycomb monolith support loaded with aluminosilicate nanozeolites can be done in a continuous mode or a batch mode with a continuous mode being preferred. The amount of time that the methanol is in contact with the aluminosilicate molecular sieve catalyst must be sufficient to convert the methanol to the desired light olefin products. The longer contact times are used at lower temperatures while shorter times are used for reaction at higher temperatures. Furthermore, when the process is carried out in a continuous mode, the weight hourly space velocity (WHSV) based on methanol can vary from about 1 hour$^{-1}$ to about 1000 hour$^{-1}$ and preferably from about 10 hour$^{-1}$ to about 100 hour$^{-1}$.

Generally, the process is carried out at elevated temperatures in order to form light olefins at a sufficiently high rate. Thus, the process should be carried out at a temperature of about 300° C. to about 600° C., preferably from about 400° C. to about 550° C. The monolithic-nanozeolite catalyst system according to the present invention records a hydrothermal stability of 25° C. to 650° C. The process may be carried out over a wide range of pressure including autogenous pressure. Thus, the pressure can vary from about 0 psig to about 250 psig, preferably from about 5 psig to about 50 psig. Preferably, the methanol to propylene conversion process is carried out in the presence of nitrogen, argon, helium, carbon dioxide and mixtures thereof, as well as an oxygen content of less than 0.01%, preferably none.

The methanol feedstock may be diluted with inert diluents in order to efficiently convert methanol into olefins. Examples of the diluents which may be used are helium, argon, nitrogen, carbon monoxide, carbon dioxide, and hydrogen and their mixtures. The amount of diluents used can vary considerably and is usually from about 5 to about 50 mole percent of the feedstock and preferably from about 25 to about 50 mole percent. In a preferred embodiment, the ratio of inert gas to hydrocarbon is in the range of 0.1-1.0, preferably 0.15-0.5, preferably 0.20-0.30, or about 0.25.

The actual configuration of the reaction zone may be any well-known catalyst reaction zone known in the art. Thus, a single reaction zone or a number of zones arranged in series or parallel may be used. In such reaction zones the methanol feedstock is flowed through a bed containing the monolith structure loaded with nanozeolite catalysts. When multiple reaction zones are used, one or more monolith structures loaded with catalyst may be used in series to produce the desired product mixture. If regeneration is required, the monolith structure loaded with catalyst can be continuously introduced as a moving bed to a regeneration zone where it can be regenerated by oxidation in an oxygen containing atmosphere to remove carbonaceous materials. Therefore, the catalyst system disclosed herein may be used in a fixed-bed reactor or a moving-bed reactor.

In one embodiment, the honeycomb monolith support structure loaded with nanozeolite crystals may be placed within or on top of a packed bed of a reactor in a vertical orientation.

In one embodiment, the packed bed consists of only the loaded honeycomb monolith structure.

In a preferred embodiment, the catalyst system has a methanol conversion selectivity towards propylene in the range of 30-90% relative to the total mass of products, preferably 35-70%, preferably 40-65%, preferably 50-60% relative to the total mass of products. In a preferred embodiment, the catalyst system has a methanol conversion selectivity towards propylene relative to the total mass of products that is greater than a substantially similar catalyst and a substantially similar process performed with substantially similar zeolite nanoparticles lacking the honeycomb monolith support, preferably at least 5% greater, preferably at least 10% greater, preferably at least 15% greater, preferably at least 20% greater, preferably at least 25% greater.

In a preferred embodiment, the catalyst system has a weight ratio of propylene to ethylene in the products of greater than 4.0, preferably greater than 4.5, preferably greater than 5.0, preferably greater than 5.5, preferably greater than 6.0, preferably greater than 6.5, preferably greater than 6.75. In a preferred embodiment, the catalyst system has a weight ratio of propylene to ethylene in the products that is greater than a substantially similar catalyst and a substantially similar process performed with substantially similar zeolite nanoparticles lacking the honeycomb monolith support, preferably at least 25% greater, preferably at least 40% greater, preferably at least 50% greater, preferably at least 60% greater, preferably at least 65% greater, preferably at least 70% greater, preferably at least 75% greater.

Figure 1C:
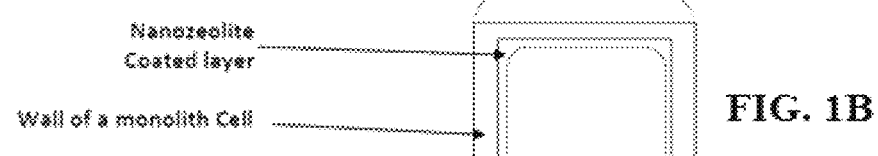
Figure 1C:
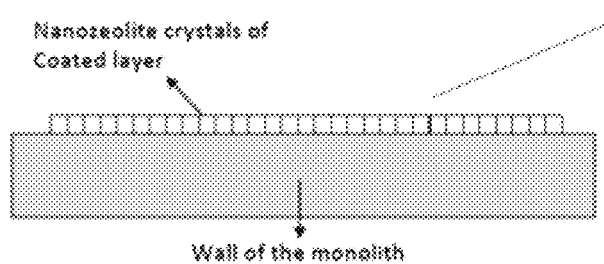

As used herein, a "honeycomb" or "honeycomb monolith" refers to natural or man-made structures that have the geometry of a honeycomb to allow the minimization of the amount of used material to reach minimal weight and minimal material cost. A honeycomb structure provides a material with minimal density and relative high out-of-plane compression properties and out-of-plane shear properties. As shown in FIG. 1, honeycomb monoliths are continuous, unitary ceramic or metallic structures, with long parallel and straight channels extended through the body, which are separated by thin walls. The geometry of honeycomb structures can vary widely but commonly feature an array of hollow cells formed between thin vertical walls. The cells may be columnar forming channels. The first monolithic structures had hexagonal-shaped passages that gave a honeycomb appearance to the cross section of the monolith. Monolithic structures that can be used in the present invention can be of different channel shapes, for example, square which is probably the most popular due its simplicity. In a preferred embodiment, the honeycomb monolith support comprises cells having an average height of 0.5-2.0 inches, preferably 0.6-1.75 inches, preferably 0.75-1.50 inches, preferably 0.9-1.2 inches and an average width of 0.5-2.0 inches, preferably 0.6-1.75 inches, preferably 0.75-1.50 inches, preferably 0.9-1.2 inches. Alternative channel or cell shapes include, but are not limited to, sinusoidal, triangular, hexagonal, trapezoidal, circular, rectangular and mixtures thereof.

Monoliths according to the present invention, for example, can be used with a honeycomb shape with 50-200 channels per square centimeter, preferably 62-186 channels per square centimeter (400-1200 cpsi=cells per square inch, wherein monoliths are preferred with a honeycomb shape with 78-171 channels per square centimeter (500-1100 cpsi), more preferably those with 93-163 (600-1050 cpsi), more preferably those having 109-155 (700-1000 cpsi), more preferably those with 124-147 (800-950 cpsi), more preferably those with 132-144 (850-930 cpsi). In an alternative embodiment, honeycombs with 8-124 channels per square centimeter (50 to 800 cpsi), preferably (150 to 700 cpsi), more preferably those having from 31 to 93 (200 to 600 cpsi), more preferably 39 to 85 (250 to 550 cpsi) and further preferably those 47 to 78 (300 to 500 cpsi), may be used. In yet another alternative embodiment, more monoliths of honeycomb shape with 54-70 channels per square centimeter (350 to 450 cpsi) may be used.

Generally catalyst systems comprise porous, inorganic structure in shaped forms such as extrudates and beads or a sintered ceramic, which is the monolith support, which serves as a substrate for active catalyst applied to it through impregnation process. The porous structure may be prepared as honeycomb, a solid matrix containing both channels and pores; foam, a solid cellular structure, non-woven fibrous structures and their combinations. A honeycomb or monolith structure is usually prepared by extrusion process. The monolith support has high pore density and thin walls which facilitate monolith catalyst system to endure the severity of the chemicals reactions for which it is used. The monolith structure may have any particular desirable configurations, but it should not hinder the flow of the reactants.

The zeolite nanoparticles according to the present disclosure may be prepared by a variety of suitable synthetic processes known to those of ordinary skill in the art. In one embodiment, the zeolite nanoparticles are formed by reacting an aluminate and a silicate and/or orthosilicate in the presence of a base to form zeolite nanoparticles having a silica to alumina molar ratio in the range of 20-5000, preferably in aqueous solution, most preferably water. In a preferred embodiment, the aluminate is sodium aluminate, the silicate and/or orthosilicate is tetraethyl orthosilicate, and the base is tetrapropyl ammonium hydroxide.

The monolith catalyst system according to the present invention may be prepared using a suitable material that is capable of resisting the reaction temperatures and pressures and is non-reacting to the selected catalyst and the reactants. Such materials include cordierite (magnesium aluminum silicate); silicon carbide, silicon nitride, silica-thoria, silica-alumina-thoria, alpha alumina, theta alumina, magnesia, metals and alloys, zirconium phosphate, silica-titania, alumina-titania and their combinations. The monolith catalyst material also may also be a composite material into which a catalyst is incorporated during its preparation.

The nanozeolite catalysts in powder form are coated on the edges and walls of the substrate using one or more coating or impregnation processes. The coating could be achieved through impregnation process in which the catalyst is deposited by dipping the substrate in a liquid mixture of zeolite and dried repeatedly. After achieving the required coating, the structure is calcined to create a strong bonding between the catalyst particles and the substrate structure.

During the reaction process, the reactant methanol is passed through the inorganic monolith structure wherein it is in contact with the catalyst deposited on the edges and walls of the structure, with the result that the desired reaction is effectively catalyzed and thus facilitated. Selection of a suitable catalyst may be made from the catalysts that are capable of catalyzing the conversion of methanol into propylene. Such catalysts are desirably further capable of impregnating or being co-formed with a given selected monolith support. Impregnation as used herein refers to the significant absorption and retention, within the pores of the ceramic, of the catalyst, the catalyst therefore being in a liquid, slurry or gaseous form prior to absorption. Such absorption is furthermore preferably such that the catalyst does not occlude the pores in such a way that the reactants are not able to efficiently flow through the monolith pores.

In a supplemental or alternative scheme, co-forming refers to incorporation of the catalyst within and throughout the inorganic matrix in conjunction with formation of the structure, by means such as co-extrusion. In either case the adherence of the catalyst to the inorganic monolith support may be facilitated by use of conventional binders, or the catalyst and monolith support materials may be selected to obtain suitable adhesion or cohesion between them.

The examples below are intended to further illustrate methods and protocols for preparing and characterizing the catalyst systems of the present disclosure. Further, they are intended to illustrate assessing the properties of these catalyst systems. They are not intended to limit the scope of the claims.

EXAMPLE 1

Preparation of the Zeolite Nanoparticles and Loading of the Honeycomb Monolith

One embodiment of the present disclosure is the variation in the silica to alumina ratio of the zeolites and its effect on propylene selectivity as well as propylene to ethylene ratio. Zeolites having silica to alumina ratios of 30, 80 and 280 were selected. These were in powder form. These zeolite samples were calcined under an air stream for activation. The zeolites can be synthesized in the laboratory or obtained from a commercial source. The following procedure was used for nanozeolite synthesis. For the targeted silica to alumina ratio, the required quantity of sodium aluminate ($NaAlO_2$) and 30 g of tetrapropyl ammonium hydroxide (TPAOH) were dissolved in 75 mL of distilled water to achieve a clear solution. To this solution, a very slow dropwise addition of tetraethyl orthosilicate (TEOS) was performed. The mixture was stirred for 24 hours to achieve a gel. The gel was then transferred to a stainless steel autoclave, which was closed and heated. The autoclave containing the gel was heated for 72 hours at 150° C. The gel was then removed and washed with distilled water and then acetone using a centrifuge. The solid zeolite material obtained was calcined at 600° C. for 8 hours.

Figure 2A:
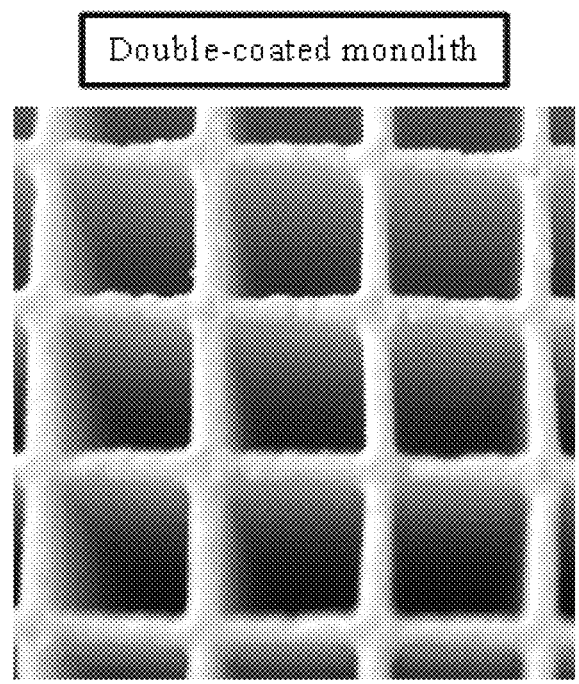
FIG. 2A is an image of a monolith honeycomb structure coated with a double layer of the nanozeolite coating.
Figure 2B:
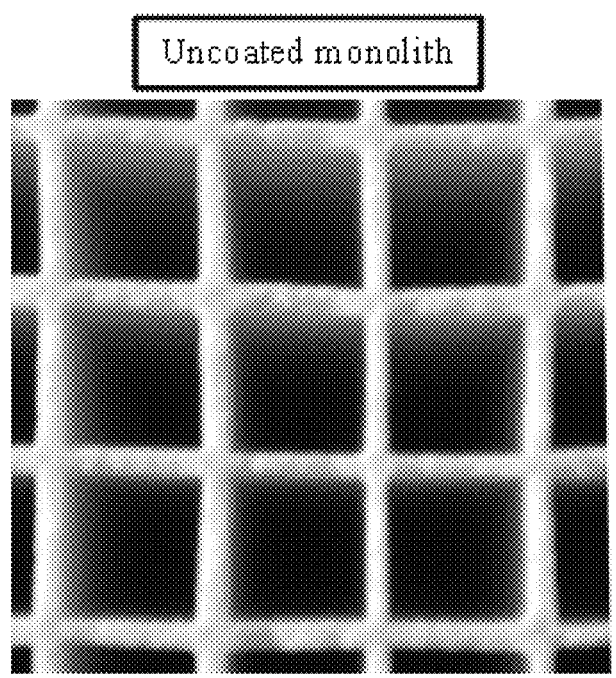
FIG. 2B is an image of the uncoated monolith honeycomb structure.

The zeolite powder was coated over the honeycomb monolith using a dip into solution method. A slurry of the zeolite was made with colloidal silica in water and thoroughly mixed into a homogeneous mixture. The monolith, having 400 cells per square inch (CPI) of the dimension 1×1 inch was dried and calcined in a furnace at 500° C. for 3 hours which was programmed at a heating rate of 5° C./min. The dried monolith was weighed at room temperature and dipped into the zeolite-colloidal silica mixture for 1 minute and removed and flushed with air to remove any loose debris present. It was then dried at room temperature and then at 120° C. for 1 hour and then calcined at 500° C. for three hours. The heating rate was 5° C. per minute. This process was repeated in the similar fashion to achieve a double coated monolith structure. An image of the double-layer coated monolith is shown in FIG. 2A and an image of the uncoated monolith is shown in FIG. 2B.

EXAMPLE 2

Evaluation of the Catalyst System for Conversion of Methanol to Light Olefins

This zeolite coated honeycomb monolith was placed in the middle of the reactor vessel. The temperature was measured in the lower center of the honeycomb monolith structure. The typical reaction conditions were as follows: the temperature was 500° C., the pressure was atmospheric pressure, the methanol feed rate was 0.32 mL/min, the nitrogen flow rate was 44 mL/min and the nitrogen to hydrocarbon ratio was 0.25. In a standard procedure the feed was then started flowing over the honeycomb monolith converting the methanol into light olefins including propylene.

Zeolite powder having a silica to alumina molar ratio of 30 (Z30), 80 (Z80) or 280 (Z280) was evaluated in a fixed-bed reactor. Prior to testing, it was calcined at 500° C. for activation, then 1.0 g of the calcined zeolite powder Z30, Z80 or Z280 was loaded in the reactor vessel having glass wool on the upper and lower sides. The zeolite catalyst evaluation was done at 500° C., atmospheric pressure, with a nitrogen flow rate of 44 mL/min, a methanol feed rate of 0.32 mL/min and at a nitrogen to hydrocarbon ratio of 0.25. The product from the reactor was collected in a gas-liquid separator; the gas sample was injected online into a gas chromatograph while the liquid product sample was collected manually. The sampling of the product was done after 150 minutes from the start of the feed time.

Figure 3:
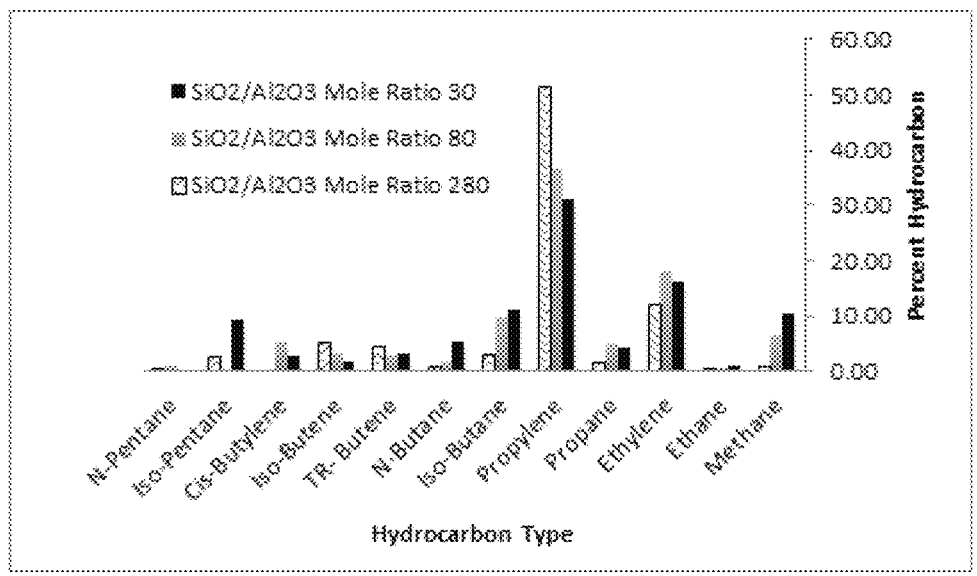
FIG. 3 is a bar graph chart illustrating the results of product percent hydrocarbon composition for the conversion of methanol to light olefins using the catalyst system comprising nanoozeolites loaded on a honeycomb monolith support of varying silica to alumina molar ratios (30, 80, or 280).

Table 1 shows a comparison of the results obtained using three zeolites of varying silica to alumina molar ratios (30, 80 or 280) and a bar graph comparison of percent hydrocarbon composition is presented in FIG. 3. The propylene selectivity was found to increase with increasing silica to alumina molar ratios in the zeolite. The results show that the zeolite Z280 produced the highest propylene yield. Based on these results, Z280 was selected for coating over the monolith structure.

TABLE 1

Comparison of percent hydrocarbon composition results achieved using zeolites having different silica to alumina molar ratios

| Hydrocarbon | $SiO_2:Al_2O_3$ Molar ratio = 30 (Z30) (%) | $SiO_2:Al_2O_3$ Molar ratio = 80 (Z80) (%) | $SiO_2:Al_2O_3$ Molar ratio = 280 (Z280) (%) |
|---|---|---|---|
| Methane | 10.3 | 6.4 | 0.7 |
| Ethane | 1.2 | 0.8 | 0.2 |
| Ethylene ($C_2$=) | 16.3 | 18.1 | 12.0 |
| Propane | 4.2 | 4.9 | 1.6 |
| Propylene ($C_3$=) | 31.0 | 36.5 | 51.6 |
| Iso-Butane | 11.2 | 9.7 | 3.2 |
| N-Butane | 5.3 | 1.8 | 1.1 |
| Trans-2-Butene | 3.1 | 3.0 | 4.5 |
| Iso-Butene | 1.7 | 3.2 | 5.3 |
| Cis-Butylene | 3.0 | 5.3 | 0.0 |
| Iso-Pentane | 9.5 | 0.0 | 2.7 |
| N-Pentane | 0.0 | 0.9 | 0.7 |
| Unknown | 0.7 | 0.4 | 1.6 |
| $C_3$=:$C_2$= ratio | 1.9 | 2.0 | 4.3 |

Figure 4:
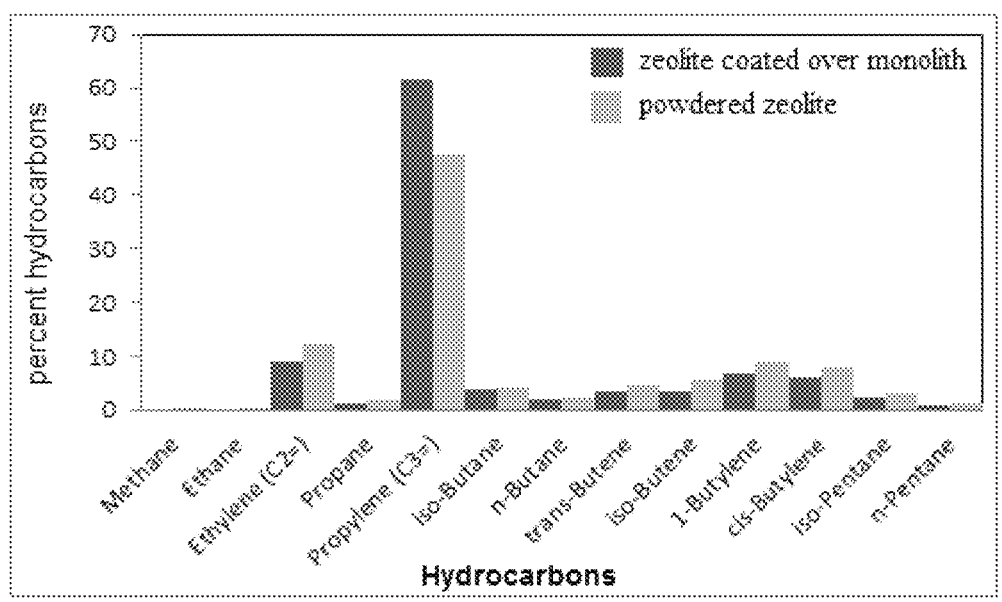
FIG. 4 is a bar graph chart illustrating the results of product percent hydrocarbon composition for the conversion of methanol to light olefins using the catalyst system comprising nanozeolites having a silica to alumina molar ratio of 280 coated over the honeycomb monolith structure or as a powder

Table 2 shows a comparison of the activity and selectivity performance of zeolite coated over the honeycomb monolith with that of powdered zeolite, a bar graph comparison of percent hydrocarbon composition is presented in FIG. 4. The data shows the advantages of zeolite coated over monolith. The yield of propylene was increased while the ethylene yield was decreased when using zeolite coated over monolith. Another advantage is the decrease in light hydrocarbons in the reaction product obtained using zeolite coated over monolith. The propylene to ethylene ratio was calculated to be 6.7 for zeolite coated over monolith as compare to 3.9 for powdered zeolite. The high performance and enhanced propylene selectivity of the catalyst system of the present disclosure comprising a honeycomb monolith structure coated with nanozeolite may be due to the large number of parallel channels which provide high contact efficiencies between the monolith and gas flow streams. In addition, the catalyst system offers a very low pressure drop, short diffusion lengths and no obstruction by particulate matter. Thus, the diffusion limitation of the monolith-nanozeolite catalyst system is significantly reduced.

TABLE 2

Comparison of percent hydrocarbon composition results achieved using zeolite coated over monolith and powdered zeolite

| Hydrocarbon | Zeolite coated over monolith (%) | Powdered Zeolite (%) |
|---|---|---|
| Methane | 0.0 | 0.3 |
| Ethane | 0.0 | 0.2 |
| Ethylene ($C_2$=) | 9.2 | 12.3 |
| Propane | 1.3 | 2.0 |
| Propylene ($C_3$=) | 61.4 | 47.7 |
| Iso-Butane | 3.8 | 4.1 |
| N-Butane | 1.9 | 2.2 |
| Trans-2-Butene | 3.3 | 4.6 |
| Iso-Butene | 3.4 | 5.6 |
| 1-Butylene | 6.6 | 9.1 |
| Cis-Butylene | 6.1 | 7.8 |
| Iso-Pentane | 2.3 | 3.0 |
| N-Pentane | 0.8 | 1.1 |
| $C_3$=:$C_2$= ratio | 6.7 | 3.9 |

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method for converting methanol into light olefins, comprising:
   passing the methanol in the vapor phase through a catalyst system for a time and at a temperature effective for converting the methanol to propylene with a selectivity towards propylene of at least 40% relative to a total mass of light olefin products and a selectivity towards propylene that is greater than a selectivity towards ethylene relative to a total mass of light olefin products and that is greater than a selectivity towards butylene relative to a total mass of light olefin products,
   wherein the catalyst system comprises:
      7-12 wt % of the zeolite nanoparticles relative to the total weight of the catalyst system of zeolite nanoparticles having a silica to alumina molar ratio of 260-5000 in the form of crystals having an average particle diameter of 10-50 nm; and
      a honeycomb monolith support with 500-1200 cells per square inch coated with the zeolite nanoparticles on the edges and inside the channels of the honeycomb monolith support;
      wherein the zeolite nanoparticles are not modified with a promoter metal.

2. The method of claim 1, wherein the zeolite nanoparticles are microporous molecular sieves having an MFI framework type, which have a BET surface area of 100-1000 $m^2g^{-1}$ and which have a pore size distribution of 0.6-1.0 nm.

3. The method of claim 1, wherein the zeolite nanoparticles have a silica to alumina molar ratio in the range of 280-2000.

4. The method of claim 1, wherein the honeycomb monolith support comprises 700-1000 cells per square inch.

5. The method of claim 1, wherein the honeycomb monolith support has an average cross-sectional dimension of 0.5-2.0 inches by 0.5-2.0 inches.

6. The method of claim 1, wherein the catalyst system further comprising a binder.

7. The method of claim 1, wherein the selectivity of the conversion towards propylene is 40-80% of the total mass of light olefin products.

* * * * *